United States Patent [19]
Pilz

[11] Patent Number: 6,143,568
[45] Date of Patent: Nov. 7, 2000

[54] METHOD FOR DETERMINING CONSTITUENTS IN WATER

[75] Inventor: Ulrich Pilz, Berlin, Germany

[73] Assignee: LAR Analytik und Umweltmesstechnik GmbH, Berlin, Germany

[21] Appl. No.: 09/103,585

[22] Filed: Jun. 24, 1998

[30] Foreign Application Priority Data

Jun. 24, 1997 [DE] Germany .......................... 197 27 839

[51] Int. Cl.⁷ .......................... G01N 25/22; G01N 33/18; G01N 31/12
[52] U.S. Cl. .......................... 436/62; 436/114; 436/125; 436/133; 436/146; 436/157; 436/160; 436/175
[58] Field of Search .................. 422/78, 79, 80; 436/62, 106, 125, 133, 155, 157, 160, 175, 181, 143, 114, 115, 145, 146

[56] References Cited

U.S. PATENT DOCUMENTS

| | | | |
|---|---|---|---|
| 4,227,887 | 10/1980 | Takahashi et al. | 23/230 |
| 5,116,736 | 5/1992 | Tahara et al. | 435/39 |

OTHER PUBLICATIONS

Derwent abstract for DE 43 44 441 C1, Jul. 1995.

*Primary Examiner*—Robert J. Warden, Sr.
*Assistant Examiner*—Kaj Olsen
*Attorney, Agent, or Firm*—Venable; George H. Spencer; Robert Kinberg

[57] ABSTRACT

A method for determining constituents in water, in particular the content of organic carbon and/or nitrogen, in which an aqueous sample is evaporated and combusted in at least one heating vessel (154a) provided with a heater (154), and the combustion product is delivered in a transporting gas stream to a detector (142) for determining the concentration of a gaseous compound of the constituent, wherein the heating vessel, or a first heating vessel, at the instant of delivery of the aqueous sample has a temperature below or at most within the range of the boiling temperature of the sample, and after delivery of the sample the temperature is increased, wherein the sample is heated by one and the same heater in a first step from an outset temperature below the boiling temperature to an evaporation temperature, and in a second step to a substantially higher temperature, and the combustion product is kept in closed circulation during the analysis.

64 Claims, 4 Drawing Sheets

METHOD FOR DETERMINING CONSTITUENTS IN WATER

BACKGROUND OF THE INVENTION

The invention relates to a method for determining constituents in water and to an apparatus for performing the method.

To determine the content of certain constituents of water—and hence the quality of water and particularly of wastewater polluted with organic substances and/or nitrogen compounds and/or halogen compounds—it is known to evaporate a sample in an atmosphere of an inert transport gas enriched with oxygen, burn it, and deliver the resultant combustion gas mixture to a detector suitable for detecting carbon dioxide, nitrogen oxides, and so forth.

Proven detectors include (among others) infrared detectors for the carbon content, special chemoluminescence detectors for the nitrogen oxide content and so-called coulometric detectors for the halide content.

Detection methods based on combusting a water sample for detecting the content of organic constituents—the so-called TOC (total organic carbon)—have gained wide use. Typically, a small amount of water with the transport gas is delivered to an oven that is heated to a predetermined temperature by a resistance heater; in the oven, it evaporates and burns virtually all at once, and the combustion gas is delivered to an NDIR-$CO_2$ detector, whose $CO_2$ content indication is a measure of the carbon content of the water sample. An advanced version of this method and corresponding apparatus are described in German Patent DE 43 44 441 C2. A modified arrangement for measuring very low TOC values—for instance in high-purity water or high-purity solutions for medical applications—is described in European Patent Disclosure EP 0 684 471 A2.

By this method, the TOC of interest is not readily determined; instead, it is in principle the total carbon content of the water (TC=total carbon) that is determined, which along with the TOC includes the component of inorganic carbon compounds (TIC=total inorganic carbon). Yet to determine the TOC, these carbon compounds are removed in a preceding stripping step; see for instance German Patent DE 39 42 229 C2 (which includes further references to the literature).

When the inorganic carbon is stripped off by expulsion, the further problem arises that expellable or volatile organic carbon (POC or VOC=volatile organic carbon) is likewise removed from the sample. In German Patent Disclosure 43 09 646 A1, a method and a testing apparatus of the above-outlined type are therefore proposed in which the POC content is measured separately and, to obtain correct POC measurement values, is caught inadvertently along with expelled carbon compounds by a special adsorber reagent.

In practical execution, on the other hand, for samples for containing solids, the total content of organic constituents cannot be determined, which additionally makes the measurement results incorrect. To avoid excessive sudden pressure loads on the analysis apparatus from deflagration in the hot oven, the water sample quantities delivered must in fact be made quite small, which necessitates the use of super-precision metering technology. To protect them, on the other hand, precision filtration of the sample must be performed, which excludes a substantial proportion of the solids, and thus the total quantity of organic constituents, from the content determination. The already only moderate detection precision, because of the small sample quantities, thus becomes unacceptably poorer for many applications, such as wastewater analysis.

In this last problem, one method provides some remedy, in which an aqueous sample is heated relatively slowly in an initially cold heating vessel and combusted in discontinuous analysis operations; see German Patent DE 44 12 778 C1. The $CO_2$ content of the combustion gas, in this discontinuous method, must be followed and integrated over a certain period of time. This method avoids major pressure fluctuations in the apparatus, and therefore larger sample quantities can be used. However, the need for following the time dependency of the $CO_2$ concentration down into the range of very low values requires a highly sensitive and correspondingly expensive detector that still functions precisely even in that range, and a precision integrator. The equipment expense is increased still further by the provision of a second heater.

BRIEF SUMMARY OF THE INVENTION

It is therefore the object of the invention to disclose an economical method, suitable for routine operation, with high measurement accuracy for the specific determination of water constituents, in particular the TOC, and an apparatus for performing the method.

The invention includes the concept of replacing the known quasi-stationary method, which is based on the evaporation and combustion of very small water quantities in an oven kept permanently at combustion temperature, with a dynamic two-stage method that has individual evaporation and combustion operations. However, thanks to a special method control, it is unnecessary to detect very low $CO_2$ concentrations, and thus there is no need to use a highly sensitive, expensive detector, either.

In an advantageous variant of the invention, it is provided that the evaporation temperature is in the range between 100° C. and 300° C., preferably between 100° C. and 150° C., and the combustion temperature is above 700° C., preferably between 800° C. and 1000° C.

The heating to the evaporation temperature may be effected in the first step approximately in a period of time of between 10 s and 200 s, and the heating to the combustion temperature may be effected in the second step within a period of time of between 5 s and 120 s. Long time periods allow relatively large sample volumes to be reacted in a way that is easy on the measurement apparatus, and they are to be preferred whenever the measurements do not require an especially short cycling time. After the first step, the temperature is advantageously kept substantially constant for a predetermined time period, preferably between 10 and 60 s.

Especially for the TOC measurement, the combustion product obtained in the second step is delivered to a $CO_2$ detector, in particular an NDIR detector for determining the carbon content. Here the steps of evaporation and combustion are preceded by a step of separating inorganic carbon compounds from the sample, in particular by acidic degassing, because they would make the $CO_2$ measurement value incorrect by indicating an overly high TOC.

In combination with the step of separating the inorganic carbon compounds, a determination of the content of inorganic carbon may be advantageously performed, in particular by delivering the degassing product to the $CO_2$ detector prior to the step of the combustion. However, if this quantification can be omitted, then these carbon compounds can also be readily precipitated out by means of a $CO_2$ collector.

If there is a need to determine the content of nitrogen compounds, then the combustion product obtained in the second step is delivered to a nitrogen detector, in particular a chemoluminescence detector, for determining the nitrogen content in the combustion gas and carrier gas mixture.

To protect the measurement apparatus against corrosion, for most practical applications the evaporation step is followed by a step of separating halide and in particular chloride ions. In combination with the separation step, it is possible as needed at the same time to perform a content determination of the halide ions—in particular by means of an electrolytic (coulometric) method and at the same time in the separation reagent.

The gas obtained in the step of the evaporation, which substantially comprises water vapor, is condensed in a cold trap into an aqueous solution, and the step of the separation of halide ions is done by means of a suitable agent, in particular $AgNO_3$ (either as a solution or in the form of silver batting) in the cold trap.

An apparatus for performing the method outlined above has as its heater a low-inertia oven, to be operated cyclically, with a low thermal mass, in particular an optical (infrared) radiant oven, which is provided with a fast-response temperature-time controller.

A suitable radiant oven has a plurality of halogen heating bars, disposed on a cylinder jacket face around the combustion vessel, and a cylindrical reflector surrounding the halogen heating bars. In an alternative version, the radiant oven has an elliptical reflector, in one focal line of which the combustion vessel is disposed, and in the other focal line of which a halogen heating bar is disposed.

The measurement apparatus overall is preferably embodied as a branching system that can be closed off from the atmosphere and that includes at least one ring line connecting the reacting or combustion vessel with the detector. In the case of embodiment for TOC determination, the apparatus also includes a degassing device, communicating on the outlet side with the detector, for the acidic degassing of the sample, and a $CO_2$ collector that can be looped into a line between the degassing device and the detector.

Other advantageous refinements of the invention are defined by the dependent claims and are described in further detail below along with the description of the preferred embodiment of the invention in conjunction with the drawings. Shown are:

BRIEF DESCRIPTION OF THE SEVERAL VIEWS OF DRAWINGS

FIG. 1, a schematic illustration of an arrangement for performing a method in a first embodiment of the invention;

FIG. 2, a schematic illustration of a modified arrangement, compared with FIG. 1, for attaining a second embodiment;

FIG. 3, a schematic illustration of a further modified arrangement for attaining a third embodiment; and FIGS. 4a and 4b, basic sketches of two embodiments of a radiant oven that can be used advantageously within the context of the embodiment of the invention.

DETAILED DESCRIPTION OF THE INVENTION

Figure 1:
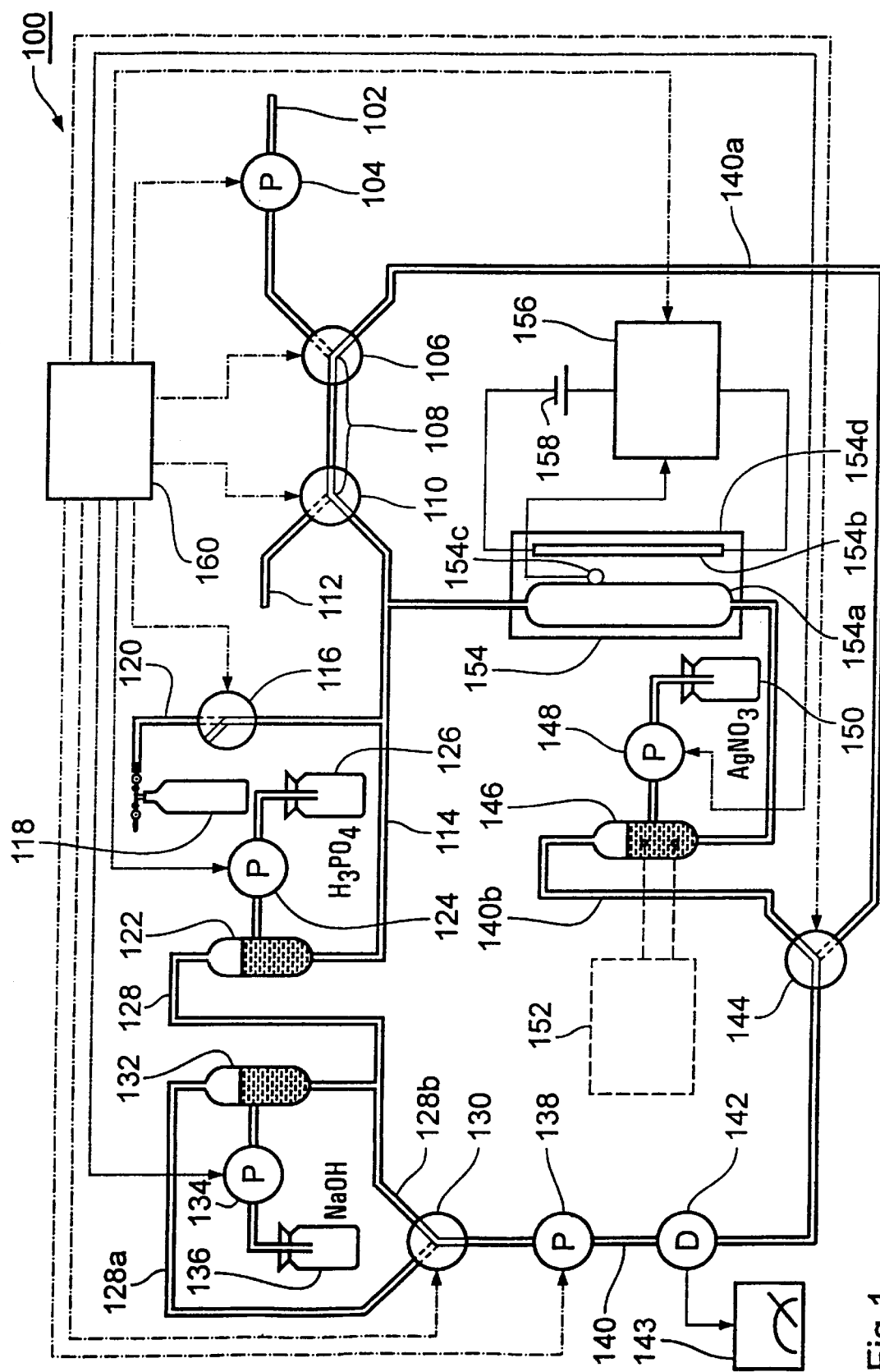

FIG. 1 shows a TOC measurement arrangement 100 for determining the total organic carbon content of a water sample (not shown in the drawing). The arrangement includes a sample intake neck 102 for taking samples via an aspirating pump 104. The sample intake neck 102 discharges downstream of the pump 104 into a two-way valve 106, which in turn discharges into a line segment 108 of exactly defined dimensions (cross section and length), which is bounded downstream by a further two-way valve 110. Aspirating sample solution by means of the aspirating pump 104 into the line segment 108, with the valve 106 open toward the intake neck 102 and the valve 110 closed, pumps a sample volume of two 2 to 5 ml, for instance, which is predetermined by the dimensions of the line segment 108, into the apparatus 100.

Extending from the valve 110 are an outlet neck 112 and a connecting line 114, into which, via a shutoff valve 166, a gas line 120 communicating with an oxygen tank 118 discharges, and which discharges in turn into a first gas washing bottle 122. The washing bottle 120, with a capacity of about 10 ml, is used for acidic degassing of the sample by means of an $H_3PO_4$ solution placed in it beforehand, which is delivered from a supply vessel 126 via a metering pump 124; see also hereinafter. Extending from the washing bottle 122 is a further connecting line 128, which branches into two line branches 128a and 128b, which lead to two connections of a further two-way valve 130. Disposed in the branch 128a is a further gas washing bottle 132, with a useful volume of about 10 ml, into which NaOH solution can be metered from a supply container 136 via a metering pump 134 and which serves—in a manner to be described in further detail below—as a $CO_2$ collector. In practice, the NaOH solution used during a measurement must be discarded afterward, which can be done by aspirating it into a collecting container; for the sake of simplicity, however, the components required for this purpose are not shown in the drawing.

The outlet of the two-way valve 130 communicates, via a feed pump 138 and a further connecting line 140 into which an NDIR $CO_2$ detector 142 is looped, with a second two-way valve 140, which discharges into two branch lines 140a and 140b. While the line 140a leads directly to the second inlet of the aforementioned two-way valve 106, a further washing bottle 146 is provided, near the valve 144 in the line 140b that discharges into the line 114, and communicates via a metering pump 148 with a supply container 150 for AgNO solution. As will be described in further detail below, this solution serves as a water vapor condenser and chloride collector and is likewise used up in the measuring process, but once again the components needed for discarding it are not shown. The chloride collector is optionally preceded by a coulometric TOX measurement device 152, known per se and shown here merely as a block drawn in dashed lines, for detecting the halide content.

Figure 4A:
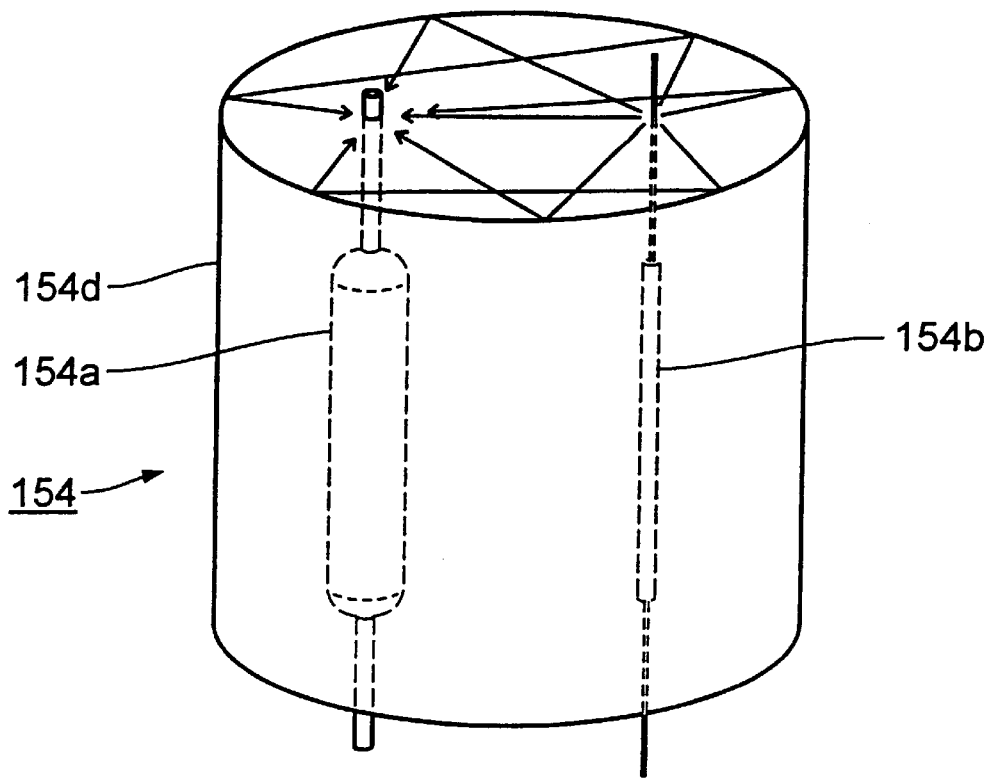

Between the condenser/chloride collector 146 and the discharge point into the line 114, a radiant oven 154 is provided for evaporating and combusting the sample. It includes a reaction vessel 154a and a heating bar 154b, which communicates with a heating current source 158 via a heating triggering means 156, and a temperature sensor 154c in a housing 154d that is reflective on the inside; see also FIG. 4a. Its outlet discharges into the aforementioned connecting line 114.

The entire apparatus is controlled by a microprocessor program controller 160. The course of the measurement method is in principle as follows:

After a previous measurement, first the used-up contents of the washing bottles 132 and 146 are discarded, and all the washing bottles 122, 132 and 146 are filled. Furthermore, the arrangement is rinsed—blocking off the line branch 140b with the chloride collector 146 and the oven via the valve 144—with oxygen with the shutoff valve 116 open and the valve 110 open to the outlet neck 112. By opening and then closing the sample valves 106 and 110 and turning on the pump 104, the line segment 108 is rinsed with a fresh sample solution, and a defined sample volume for the measurement is furnished.

Next, the sample aspirating valve 106 and the $O_2$ valve 116 are closed, and the line segment 108 containing the sample is looped into the arrangement by opening the valve 110 toward the line 114; the valve 130 is open toward the line branch 128, and the valve 144 is open toward the line branch 140a, and thus the line branches 128a and 140b remain blocked off. Turning on the feed pump 138 pumps the sample into the scrubber bottle 122 for the acidic degassing.

On flowing through the $H_3PO_4$ solution, the inorganic carbon compounds (dissolved $CO_2$, $H_2CO_3$, hydrogen carbonates and carbonates) that yield the TIC and are contained in the sample are converted into $CO_2$ dissolved in the sample water. The thorough mixing with the oxygen in the line system brings about the so-called stripping; that is, the $CO_2$ is converted to the gas phase and can be detected in that phase by the infrared detector 140. In this way, the TIC content of the sample can be determined first. If the exact volume of the gas circulation loop is known, then the TIC can be quantified, in the sense of an absolute measurement.

Next, by connecting the valve 136 to the lie branch 128a, the $CO_2$ collector 132 is incorporated into the loop and at the same time the "bypass" 128b is blocked off, thereby removing the $CO_2$ from the gas in the loop. If there is no need to detect the TIC separately, then work can be done with this valve position from the outset, thus saving analysis time.

If the loop gas, via the acidic degassing and the $CO_2$ collector, is completely cleaned of inorganic carbon (which can be monitored at the $CO_2$ detector 140 or determined from the course of a period of time required by experience), then the $CO_2$ collector is turned off again by reversing the valve 130 again, and the line branch 140b, instead of the line branch 140a, is connected into the loop along with the oven 154 and the chloride collector 146 by reversing the valve 144. Turning on the feed pump 138 with a reversed pumping direction forces the TIC-free sample, including the phosphoric acid put in place beforehand, into the oven 154. Then there is initially a wait until the $CO_2$ base value at the $CO_2$ detector 140 is stabilized. (This can be done either by human operators or by means of an automatic measurement value comparison via the controller 160. In the latter case, naturally there must be a data connection from the detector 142 to the controller 160.)

Next, under program control by the controller 160 and the heating controller 156, the oven 154 is first heated to a first temperature for relatively slow evaporation of the water (such as 120° C.). The water vapor is condensed in the condenser/chloride collector 146 and at the same time is freed of $Cl^-$ ions, by precipitating out AgCl, in order to guard the arrangement against corrosion. $I^-$ and Br ions can also be bound in the same way. Once the evaporation has concluded, after 10 to 200 seconds, the oven is heated in a second heating phase to 800 to 900° C. within a few seconds, and as a result, within about 30 seconds, the portion of the sample that has remained after the evaporation of the water is combusted.

Once again, the $Cl^-$ and optionally other halide ions are bound in the chloride collector 146.

In the course of the evaporation and ensuing combustion, the total organic carbon components of the sample (TOC, including the volatile components or VOC) are converted into $CO_2$ and detected in an integrated fashion in the NDIR detector 142. Since the gas loop volume and the sample volume are known, an absolute measurement with high accuracy is possible. By means of the integrating measurement in the closed sample/gas loop, the necessity, which exists in the prior art, of precise detection of very low $CO_2$ concentrations in the fadeout range of combustion, and thus the use of an expensive, highly sensitive detector, or averted.

Figure 4B:
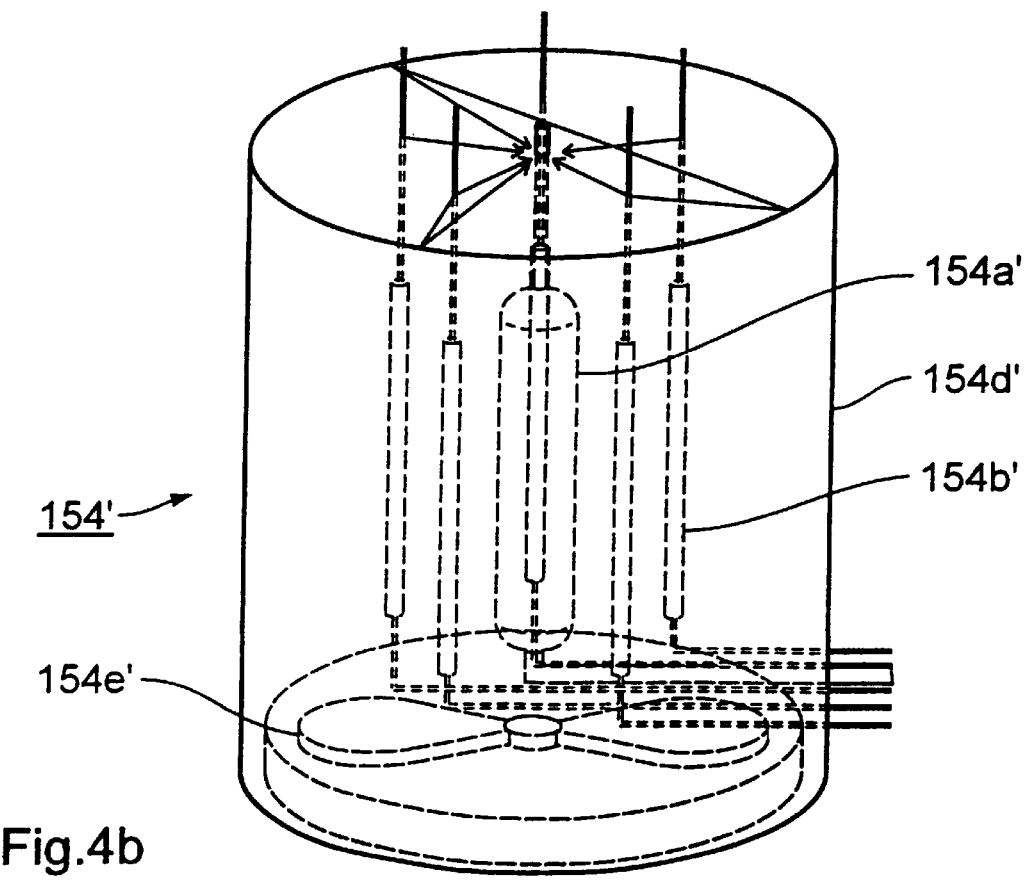

Because of its low thermal mass, the radiant oven 154 cools rapidly and is ready for a new measurement operation, which makes short measurement cycle times possible. It may additionally have a blower for even faster cooling down, as shown in FIG. 4b. In principle, however, some other oven of low thermal inertia can also be used in the arrangement 100.

Figure 2:
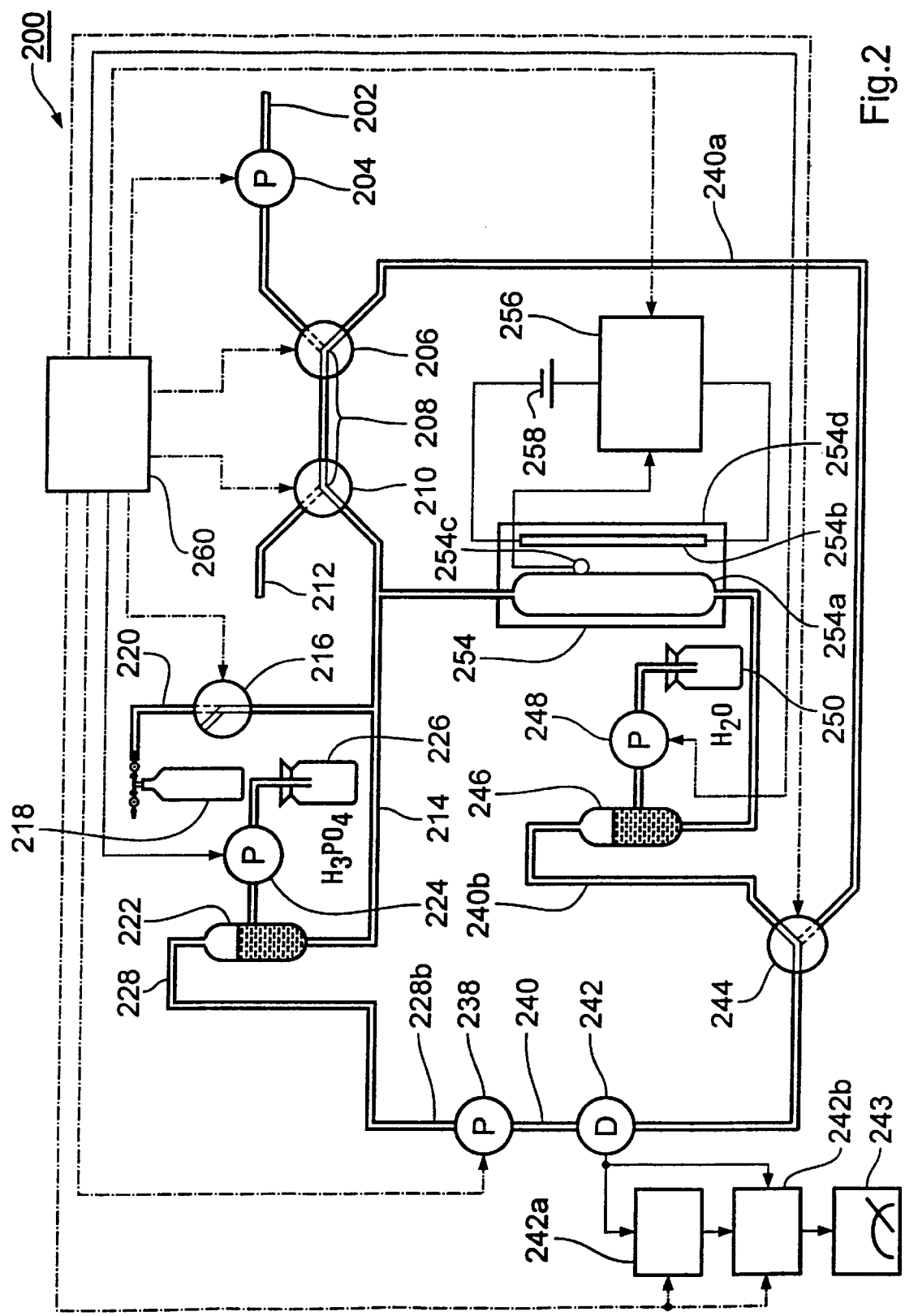
Figure 3:
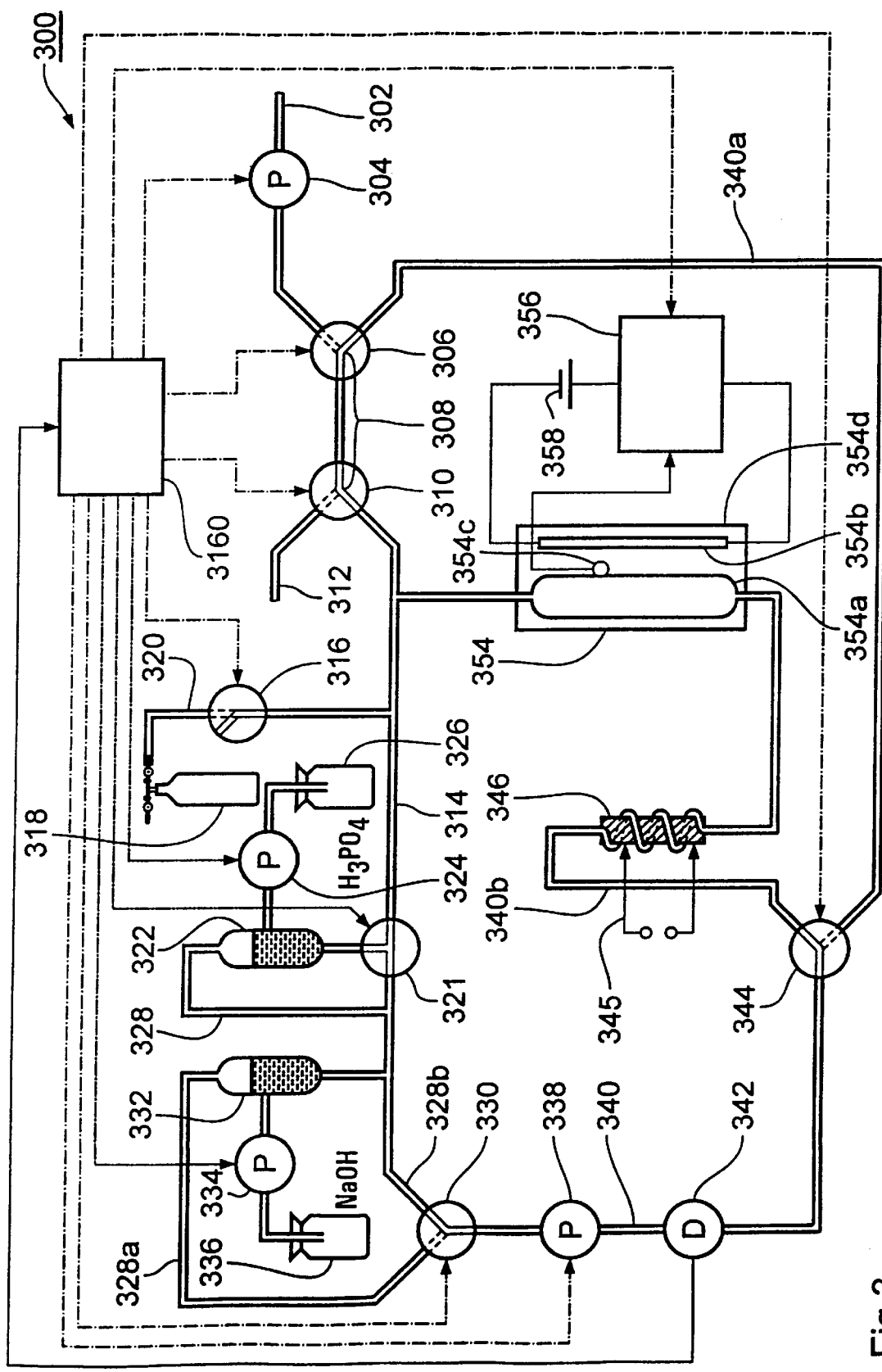

In FIGS. 2 and 3, modifications of the arrangement described above are shown, in which identical or similar elements to those of FIG. 1 are designated by corresponding numerals and will not be described again below.

The measurement arrangement 200 of FIG. 2 is simplified in its construction, first in that the $CO_2$ collector with its accessory parts and the corresponding line branch and the associated two-way valve are omitted. The TIC as a base signal is necessarily then included in the $CO_2$ measurement values here. However, since by the above procedure the TIC can be determined separately prior to the step of evaporation and combustion of the sample, in which arrangement it is possible to determine the TOC subtractively, to which end the detector is additionally assigned a measurement value memory 142a and a subtraction stage 142b, which are controlled via the controller 160. The washing bottle 146 also acts here solely as a cold trap and is filled not with $AgNO_3$ but, in a way that saves operating costs, with (highly pure) water. Accordingly, intrinsically no device for determining the halide content (TOX) is provided, either.

In the measurement arrangement 300 of FIG. 3, the washing bottle 146 of FIG. 1, acting as a condenser and chloride collector, is replaced with a cooling body 346 with a Peltier cooler 345, and the $CO_2$ measurement values are set from the IR spectrometer 342 to a control and processing unit 360 for processing and outputting. In a further (NDIR) detector modification, which also enables $CL^-$ stripping, the cooled tube portion can be filled with silver batting. In the arrangement 300, one additional magnet valve 321 between the line segments 314 and 328b makes it possible intermittently to circumvent the acidic degassing, and thus it is possible, separately from the TOC, to detect the volatile carbon components (VOC) in an additional measurement step.

In its embodiment, the invention is not limited to the preferred exemplary embodiments described above. On the contrary, a number of variants that make use of the provisions described, even in differently designed embodiments, are conceivable.

For instance, it is not absolutely necessary to use a single evaporation and combustion vessel; instead, the heating of the sample can also be done in two separate vessels or "ovens", of which the first has a low-inertia, controllable heater along the lines of the above description, while the second—which is used for the actual combustion—is preferably kept substantially at constant temperature. The temperature of the first vessel is then varied between an evaporation temperature and a temperature (preferably above about 400° C.) located markedly above it.

In addition, in particular the actual combustion vessel, that is, the only or the second heating vessel, may have a catalyst (such as Be) that is bonded to a substrate.

Furthermore, essential parts of the described arrangements—with a nitrogen oxide detector operating on the basis of chemoluminescence, for instance, instead of the $CO_2$ detector or in addition to it—can be used in a similar way to determine the total nitrogen content (TN) of a water sample.

An NDIR spectrometer need not necessarily be used as the $CO_2$ detector; alternatively, for instance, the $CO_2$ can be converted into carbonic acid and a pH sensor can be used.

What is claimed is:

1. An analysis method for determining at least one of organic carbon and nitrogen constituents in water, comprising the steps of:

delivering an aqueous sample to a heating vessel comprising a heater, wherein the heating vessel at the instant of delivery of the aqueous sample has a temperature up to about the boiling temperature of the sample;

evaporating the aqueous sample, wherein the sample is heated by said heater from an outset temperature below the boiling temperature to an evaporation temperature, said evaporation temperature being substantially below a combustion temperature;

combusting the evaporated sampled, wherein the sample is heated by said heater to the combustion temperature to yield a combustion product; and delivering the combustion product in a transporting gas stream to a detector for determining the concentration of a gaseous compound of the constituent, wherein the combustion product is kept in closed circulation during the analysis.

2. The method of claim 1, wherein precisely one heating vessel embodied as a combustion vessel is used, and the temperature in the combustion step is increased to a combustion temperature.

3. The method of claim 2, wherein the evaporation temperature is in the range between 100° C. and 300° C. and the combustion temperature is above 700° C.

4. The method of claim 2, wherein the heating to the evaporation temperature is effected in the evaporation step in a period of time of between 10 s and 200 s, and the heating to the combustion temperature is effected in the combustion step within a period of time of between 5 s and 120 s.

5. The method of claim 2, wherein the evaporation temperature is between 100° C. and 150° C., and the combustion temperature is between 800° C. and 1000° C.

6. The method of claim 1, wherein the evaporation and combustion steps are performed in a first heating vessel, and an additional combustion step is performed in a second heating vessel, embodied as a combustion vessel, which is kept substantially at constant combustion temperature.

7. The method of claim 1, wherein the temperature is kept substantially constant for a predetermined time period following the evaporation step.

8. The method of claim 1, wherein the combustion product obtained in the combustion step is delivered to a $CO_2$ detector for determining the carbon content.

9. The method of claim 8, wherein the steps of evaporation and combustion are preceded by a step of separating inorganic carbon compounds from the sample.

10. The method of claim 9, wherein the step of separating the inorganic carbon compounds further comprises a determination of the content of inorganic carbon.

11. The method of claim 10, wherein the determination of the content of inorganic carbon further comprises delivering the degassing product to the $CO_2$ detector prior to the step of the combustion.

12. The method of claim 9, wherein the separation step comprises acidic degassing.

13. The method of claim 8, wherein the $CO_2$ detector is a non-dispersive infra-red (NDIR) detector.

14. The method of claim 1, wherein the combustion product is delivered to a nitrogen detector.

15. The method of claim 14, wherein the nitrogen detector is a chemoluminescence detector.

16. The method of claim 1, wherein the step of evaporation is followed by a step of separating at least one of halides and halide ions from the sample.

17. The method of claim 16, wherein the step of the separation further comprises a determination of the content of halide ions.

18. The method of claim 17, wherein the content of the halide ions is determined by a coulometric method.

19. The method of claim 16 wherein the step of the separation of halides is done in a suitable agent in the cold trap.

20. The method of claim 19, wherein the suitable agent is one of Ag or $AgNO_3$.

21. The method of claim 16, wherein the halides separating step comprising separating chloride ions.

22. The method of claim 1, wherein the gas obtained in the step of the evaporation, which substantially comprises water vapor, is condensed in a cold trap.

23. An analysis method for determining at least one of organic carbon and nitrogen constituents in water, comprising the steps of:

delivering an aqueous sample to a heating vessel, wherein the heating vessel at the instant of delivery of the aqueous sample has a temperature up to about the boiling temperature of the sample;

separating inorganic carbon compounds from the sample;

evaporating the aqueous sample after the inorganic carbon compound separating step, wherein the sample is heated from an outset temperature below the boiling temperature to an evaporation temperature, said evaporation temperature being substantially below a combustion temperature;

combusting the evaporated sampled, wherein the sample is heated to the combustion temperature to yield a combustion product; and delivering the combustion product in a transporting gas stream to a detector for determining the concentration of a gaseous compound of the constituent, wherein the combustion product is kept in closed circulation during the analysis.

24. The method of claim 23, wherein precisely one heating vessel embodied as a combustion vessel is used, and the temperature in the combustion step is increased to a combustion temperature.

25. The method of claim 24, wherein the evaporation temperature is in the range between 100° C. and 300° C. and the combustion temperature is above 700° C.

26. The method of claim 24, wherein the evaporation temperature is in the between 100° C. and 150° C., and the combustion temperature is between 800° C. and 1000° C.

27. The method of claim 24, wherein the heating to the evaporation temperature is effected in the evaporation step in a period of time of between 10 s and 200 s, and the heating to the combustion temperature is effected in the combustion step within a period of time of between 5 s and 120 s.

28. The method of claim 23, wherein the evaporation and combustion steps are performed in a first heating vessel, and an additional combustion step is performed in a second heating vessel, embodied as a combustion vessel, which is kept substantially at constant combustion temperature.

29. The method of claim 23, wherein the temperature is kept substantially constant for a predetermined time period following the evaporation step.

30. The method of claim 23, wherein the combustion product obtained in the combustion step is delivered to a $CO_2$ detector for determining the carbon content.

31. The method of claim 30, wherein the $CO_2$ detector is an NDIR detector.

32. The method of claim 23, wherein the inorganic carbon compound separation step comprises acidic degassing.

33. The method of claim 23, wherein the step of separating the inorganic carbon compounds further comprises a determination of the content of inorganic carbon.

34. The method of claim 33, wherein the determination of the content of inorganic carbon further comprises delivering the degassing product to the $CO_2$ detector prior to the step of the combustion.

35. The method of claim 23, wherein the combustion product is delivered to a nitrogen detector.

36. The method of claim 35, wherein the nitrogen detector is a chemoluminescence detector.

37. The method of claim 23, wherein the step of evaporation is followed by a step of separating halides from the sample.

38. The method of claim 37, wherein the halides separating step comprising separating chloride ions.

39. The method of claim 37, wherein the halides separating step further comprises a determination of the content of halide ions.

40. The method of claim 39, wherein the content of the halide ions is determined by a coulometric method.

41. The method of claim 23, wherein the gas obtained in the step of the evaporation, which substantially comprises water vapor, is condensed in a cold trap.

42. The method of claim 41, wherein the step of the separation of halides and halide ions is done in a suitable agent in the cold trap.

43. The method of claim 42, wherein the suitable agent is one of Ag or $AgNO_3$.

44. An analysis method for determining at least one of organic carbon and nitrogen constituents in water, comprising the steps of:

delivering an aqueous sample to a heating vessel, wherein the heating vessel at the instant of delivery of the aqueous sample has a temperature up to about the boiling temperature of the sample;

evaporating the aqueous sample, wherein the sample is heated from an outset temperature below the boiling temperature to an evaporation temperature, said evaporation temperature being substantially below a combustion temperature;

separating, after the evaporating step, at least one of halides and halide ions from the sample;

combusting the evaporated sample, wherein the sample is heated to the combustion temperature to yield a combustion product; and delivering the combustion product in a transporting gas stream to a detector for determining the concentration of a gaseous compound of the constituent, wherein the combustion product is kept in closed circulation during the analysis.

45. The method of claim 44, wherein precisely one heating vessel embodied as a combustion vessel is used, and the temperature in the combustion step is increased to a combustion temperature.

46. The method of claim 45, wherein the evaporation temperature is in the range between 100° C. and 300° C. and the combustion temperature is above 700° C.

47. The method of claim 45, wherein the evaporation temperature is in the between 100° C. and 150° C., and the combustion temperature is between 800° C. and 1000° C.

48. The method of claim 45, wherein the heating to the evaporation temperature is effected in the evaporation step in a period of time of between 10 s and 200 s, and the heating to the combustion temperature is effected in the combustion step within a period of time of between 5 s and 120 s.

49. The method of claim 44, wherein the evaporation and combustion steps are performed in a first heating vessel, and an additional combustion step is performed in a second heating vessel, embodied as a combustion vessel, which is kept substantially at constant combustion temperature.

50. The method of claim 44, wherein the temperature is kept substantially constant for a predetermined time period following the evaporation step.

51. The method of claim 44, wherein the combustion product obtained in the combustion step is delivered to a $CO_2$ detector for determining the carbon content.

52. The method of claim 51, wherein the $CO_2$ detector is a non-dispersive infra-red (NDIR) detector.

53. The method of claim 51, wherein the steps of evaporation and combustion are preceded by a step of separating inorganic carbon compounds from the sample.

54. The method of claim 53, wherein the inorganic carbon compound separation step comprises acidic degassing.

55. The method of claim 53, wherein the step of separating the inorganic carbon compounds further comprises a determination of the content of inorganic carbon.

56. The method of claim 55, wherein the determination of the content of inorganic carbon further comprises delivering the degassing product to the $CO_2$ detector prior to the step of the combustion.

57. The method of claim 44, wherein the combustion product is delivered to a nitrogen detector.

58. The method of claim 57, wherein the nitrogen detector is a chemoluminescence detector.

59. The method of claim 44, wherein the halide separating step comprising separating chloride ions.

60. The method of claim 44, wherein the halide separating step further comprises a determination of the content of halide ions.

61. The method of claim 60, wherein the content of the halide ions is determined by a coulometric method.

62. The method of claim 44, wherein the gas obtained in the step of the evaporation, which substantially comprises water vapor, is condensed in a cold trap.

63. The method of claim 62, wherein the step of the separation of halide ions is done in a suitable agent in the cold trap.

64. The method of claim 63, wherein the suitable agent is one of Ag or $AgNO_3$.

* * * * *